United States Patent [19]

Fitzjarrell

[11] Patent Number: 5,449,517
[45] Date of Patent: Sep. 12, 1995

[54] METHOD AND FORMULATION FOR ELIMINATING FLEAS ON ANIMALS

[76] Inventor: Edwin A. Fitzjarrell, P.O. Box 3600, Sisters, Oreg. 97759

[21] Appl. No.: 155,215

[22] Filed: Nov. 22, 1993

[51] Int. Cl.⁶ .............................................. A61K 35/78
[52] U.S. Cl. .................... 424/195.1; 424/DIG. 10; 424/405; 514/919
[58] Field of Search ................. 424/195.1, DIG. 10, 424/405; 514/919

[56] References Cited

U.S. PATENT DOCUMENTS

| | | | |
|---|---|---|---|
| 4,374,853 | 2/1983 | Workman | 424/303 |
| 5,009,890 | 4/1991 | Dipoppo | 424/195.1 |
| 5,096,709 | 3/1992 | VanderSloot | 424/195.1 |
| 5,260,341 | 11/1993 | Rajamannan | 514/675 |
| 5,314,699 | 5/1994 | Baden | 424/660 |

OTHER PUBLICATIONS

Agricultural Economics Discussion Paper, Department of Agriculture, University of Queensland, (1988), 64 pages, 70 references, 1 app. (Abstract only).
Lewis, Medical Botany, Wiley & Sons, N.Y., p. 366, 1977.
The Merck Index, No. 7242, 9th Ed., 1976.
Bassett et al., Med. J. Aust., 153:455–58, 1990.

*Primary Examiner*—John W. Rollins
*Attorney, Agent, or Firm*—John R. Duncan; Frank D. Gilliam; Donn K. Harms

[57] ABSTRACT

A formulation for treating animals such as dogs, cats, hamsters, white rats, etc. to reduce or eliminate fleas on the animal. The basic mixture comprises a suitable quantity of tea tree oil (an essential oil of the Australian native tree *Melaleuca alternifolia*) in a water carrier. The liquid is rubbed into the fur of the flea infested animal, preferably to the point where the fur and underlying skin is damp but not dripping wet. The tea tree oil has been found to have additional beneficial properties, in reducing infection and promoting healing of scratches and sores caused by the animal scratching the fleas. Other ingredients may be included, such as mild soaps, surfactants and diluting agents, to provide other benefits. The tea tree oil, as an oil, will help relieve overly dry skin characteristic of dry, desert-like regions and can be used frequently, if desired, without leaving the animal with dry skin or eczema.

8 Claims, No Drawings

METHOD AND FORMULATION FOR ELIMINATING FLEAS ON ANIMALS

BACKGROUND OF THE INVENTION

This invention relates in general to reducing or eliminating flea infestations on household pets and the like and, more specifically, to a formulation which both kills fleas and improves the condition on the skin of an animal.

Fleas are small, wingless insects that live on mammals and birds and suck blood for food. Fleas are dangerous pests because they can carry the germs that cause plague and typhus. While some types of fleas live on only certain types of animals, most pass freely from animals to human beings and from animal to animal. Besides the threat of disease transmission, fleas cause itching that results in animals scratching to the point that open wounds or sores may result, leading to secondary bacterial infections. A great many different types of flea deterring or killing treatments have been developed in attempts to rid animals of fleas.

A variety of chemicals have been manufactured and sold for use in killing fleas that infest various animals, in particular household pets such as dogs, cats, hamsters, etc. Most are harsh, man-made chemicals that can have serious consequences where used too often or in excess of recommended quantities. Typical of these chemicals are propoxur (o-isopropoxphenyl) methyl carbamate, d-Limonene, cyano(3-pheoxypheny)methyl 4-chroro-alpha (i-methylethyl)beneneacetate, pyrethrine, piperonyl butoxide and N-octyl bicycloheptane dicarboximide. While generally effective against fleas if very carefully used, these chemicals often have serious side effects. Many excessively dry the skin or cause eczema or allergic reactions in some animals, a serious problem in dry areas, such as the desert-like band from Southern California through Texas. Scratches and sores caused by the animal scratching at fleas can become infected and the infections are often aggravated by these chemicals. Many of these chemicals cannot be applied to the fur of animals, such as cats, that self-groom by licking the skin and fur.

Persons applying these flea killing chemicals to animals must often be very carefully to avoid excessive contact with them. Those grooming animals must often wear rubber gloves to avoid continuous contact with the chemicals. Care must be exercised in keeping the chemicals out of the eyes and away from the mucus membranes of both the animal and the person applying them. Breathing vapor from the chemicals over long periods must be avoided. Many of these chemicals are not rapidly biodegradeable and constitute an environmental hazard if misused.

Thus, there is a continuing need for improved materials that can be applied to fur bearing animals to eliminate fleas while being environmentally benign, avoiding deleterious side effects and, and preferably actually improving the skin condition of the animal and reducing infection of scratches and sores.

SUMMARY OF THE INVENTION

The above noted problems, and others, are overcome by a method and composition for killing fleas that basically involves mixing suitable quantities of tea tree oil with a water carrier and applying the mixture to the fur and skin of a flea infested animal. Tea tree oil is an essential oil of the Australian native tree *Melaleuca alternifolia*. Aloe extract is desirably included as a beneficial agent to the skin. In many cases, the inclusion of from about 1 to 5 volume percent of a soap, preferably a mild, non-allergenic, soap of the sort sold for use by human beings as a "face soap" is beneficial While any suitable proportion of tea tree oil may be used, with up to about 50% by volume being effective and without significant disadvantageous side effects, for optimum performance, ease of application and economy, from about 2 to 10% by volume tea tree oil is preferred. For optimum results with most animals, about 3 volume per cent tea tree oil is used. The formulation may be applied as often as required, depending upon the severity of the infestation and the opportunities for re-infestation once the carried fleas have been eliminated. The treatment may be done as often as every 2 to 3 days if necessary, although treatment once every 5 to 7 days is generally effective. Prior art chemical treatments generally require at least about 7 to 10 days between treatments to avoid skin damage. The mixture may be applied in any suitable manner, with spraying from a hand-held pump-type sprayer being most effective and convenient.

This formulation has the further advantageous characteristic of protecting the skin against infection and promoting healing of scratches or sores caused by scratching at fleas. Tea tree oil in the form of a gel has been used as a bactericidal agent to promote healing in burn treatment, as described by Ascanio in U.S. Pat. No. 5,009,890. Reduction of the number of inflamed and non-inflamed acne lesions and fewer side effects than other agents through the application of a tea tree oil gel was described by Bassett et al. in The Medical Journal of Australia, Vol 153, pp. 455–458, Oct. 15, 1990.

Other additives may be included in the mixture, if desired, to accomplish ancillary purposes. For example, from about 1 to 30 volume percent of aloe vera gel may be desirable to further enhance skin condition. While any suitable aloe species may be used, Aloe vera, Aloe barbadensis and Aloe ferox have been most thoroughly investigated and are most likely to avoid undesirably side effects.

Other additives that may be desirable in some cases include mild soaps, surfactants, peppermint oil and mixtures thereof. While any suitable amount of the formulation may be applied, in general applying just enough to dampen the fur and skin is most effective. While the fur could be wet to a dripping condition, in general the additional quantity does not significantly increase treatment effectiveness. Care should be exercised with cats or other animals that tend to lick the fur to begin with lower quantities on the chance that a particular animal might have an unusual sensitivity to any ingredient used in the formulation.

In tests with this treatment on dogs, when compared to untreated dogs and dogs treated with prior art chemical agents, the tea tree oil treatment is found to be fully effective in severely limiting or eliminating the number of fleas present over the next few days after treatment. Skin dryness is significantly reduced and scratches and sores heal rapidly. The untreated dogs continue to have severe flea infestations and significant skin problems with scratches and sores caused by scratching. A reduction in the number of fleas on dogs treated with the prior art chemicals is also noted; however, those dogs continue to have skin problems including dryness, flaking skin and slowly healing sores.

Additional tests with cats, hamsters, gerbles and mice show similar results.

Other applications, variations and ramifications of this invention will occur to those skilled in the art upon reading this disclosure. Those are intended to be included within the scope of this invention, as defined in the appended claims.

I claim:

1. The formulation for killing fleas on fur bearing animals while improving skin condition which comprises a mixture of from about 2 to 10 volume per cent tea tree oil, from about 1 to 30 volume per cent aloe vera gel, from about 1 to 5 volume per cent soap and water.

2. The formulation according to claim 1 wherein said mixture contains about 3 volume per cent tea tree oil.

3. The formulation according to claim 1 wherein said aloe is extracted from an aloe vera gel selected from the group consisting of aloe vera, aloe barbadensis, aloe ferox and mixtures thereof.

4. The method of killing fleas on a fur bearing animal while improving skin condition which comprises the steps of:

providing a mixture comprising from about 2 to 10 volume percent tea tree oil and water;

applying said mixture to the hair and skin of a flea infested fur bearing animal; and continuing said application until the skin and fur is at least substantially uniformly dampened.

5. The method according to claim 4 wherein about 3 volume per cent tea tree oil is used.

6. The method according to claim 4 wherein from about 1 to 30 volume per cent aloe vera gel is included in said mixture.

7. The method according to claim 6 wherein said aloe vera gel is selected from extracts of aloe vera, aloe barbadensis, aloe ferox and mixtures thereof.

8. The method according to claim 7 wherein said mixture includes from about 1 to 5 volume percent soap.

* * * * *